(12) United States Patent
Baird (10) Patent No.: US 10,123,883 B2
(45) Date of Patent: Nov. 13, 2018

(54) LENGTH/OFFSET REPRODUCING DEVICE FOR TOTAL HIP ARTHROPLASTY

(71) Applicant: Karl Baird, Centerville, IN (US)

(72) Inventor: Karl Baird, Centerville, IN (US)

( * ) Notice: Subject to any disclaimer, the term of this patent is extended or adjusted under 35 U.S.C. 154(b) by 477 days.

(21) Appl. No.: 14/805,646

(22) Filed: Jul. 22, 2015

(65) Prior Publication Data

US 2017/0020686 A1    Jan. 26, 2017

(51) Int. Cl.
  *A61B 17/58*   (2006.01)
  *A61B 17/60*   (2006.01)
  *A61F 2/00*    (2006.01)
  *A61F 2/46*    (2006.01)

(52) U.S. Cl.
  CPC ................... *A61F 2/4607* (2013.01)

(58) Field of Classification Search
  CPC combination set(s) only.
  See application file for complete search history.

(56) References Cited

U.S. PATENT DOCUMENTS

| | | | |
|---|---|---|---|
| 4,959,066 A | * | 9/1990 | Dunn ................. A61B 17/15 606/87 |
| 5,122,145 A | | 6/1992 | Fishbane |
| 5,318,571 A | | 6/1994 | Benson |
| 5,578,037 A | | 11/1996 | Sanders |
| 5,782,091 A | | 7/1998 | Nakajima |
| 6,258,097 B1 | | 7/2001 | Cook |
| 8,588,892 B2 | | 11/2013 | Hladio |
| 8,611,504 B2 | | 12/2013 | Kubiak |
| 2009/0048603 A1 | | 2/2009 | Hoag |
| 2009/0222015 A1 | | 9/2009 | Park |
| 2012/0116468 A1 | | 5/2012 | Beverland |
| 2012/0123423 A1 | | 5/2012 | Fryman |
| 2013/0116699 A1 | | 5/2013 | Smith |

* cited by examiner

*Primary Examiner* — Sameh Boles
(74) *Attorney, Agent, or Firm* — Woodard, Emhardt, Moriarty, McNett & Henry LLP (57) ABSTRACT

A guide device for assessing the length and offset of a hip of a patient is disclosed. The guide device includes an overlay portion and an alignment portion. The overlay portion is configured to enable assessment of the relative location of the guide device to the original femoral head of a patient using a marking on the overlay portion. Reference points for positioning the guide device are created on the femur. When the guide device is positioned at the reference points it can be used to position a replacement femoral head in the same position as the patient's original femoral head by aligning the replacement femoral head with the marking on the overlay portion.

13 Claims, 6 Drawing Sheets

LENGTH/OFFSET REPRODUCING DEVICE FOR TOTAL HIP ARTHROPLASTY

BACKGROUND

Total hip arthroplasty (hip replacement surgery) involves replacement of both the ball and the socket sides of the hip joint. The ball portion of the patient's hip, the femoral head, is replaced with an artificial ball. The patient's socket, the acetabulum, is covered with an artificial socket liner. When replacing the hip, it is important for the surgeon to be able to judge the length and offset of the original femoral head and match the position of the artificial femoral head to the position of the original. Creating the correct offset and length with the replacement femoral head is important for avoiding leg length discrepancy and for hip stability and strength.

Some measurement devices attempt to measure the length and offset of the hip from a fixed position on the pelvis. This process usually involves driving a metal pin into the pelvis bone as a point of reference for measurements comparing the original hip to the replacement. However, these measurement techniques can be time consuming and difficult to keep accurate. Also, there is a risk of injury when inserting the pin into the pelvis. It would be desirable to provide a device that can accurately measure the offset and length of a patient's hip that is quick and easy to use and that also does not include an additional risk of injury.

Thus, there is a need for improvement in this field.

SUMMARY

The claims and only the claims recite the invention. In summary, it may include a guide device for assessing the length and offset of a hip of a patient. The guide device may have an overlay portion configured to enable assessment of the relative location of the guide device to the original femoral head of a patient. The relative location is indicated by a marking on the overlay portion. The guide device also includes an alignment portion including a contact surface. The contact surface is configured to contact the femur of a patient and create at least two reference points for positioning the guide device on the femur. When the contact surface of the alignment portion is positioned at the reference points, the guide device can be used to position a replacement femoral head in the same position as the original femoral head by aligning the replacement femoral head with the marking on the overlay portion.

In some embodiments, the guide device may include an overlay portion with a line system that may be used to determine the relative location of the original femoral head of the patient. The guide device has an alignment portion configured to physically engage a portion of the femur of the patient. The alignment portion includes at least one contact surface that extends obliquely from the alignment portion. The contact surface is configured to be inserted into a groove cut into the femur to create a reference point for positioning the guide device. The guide device can be used to position an artificial femoral head in the same relative position as the original femoral head by positioning the contact surface at the same reference points on the femur and aligning the artificial femoral head with the marking on the overlay portion.

Some embodiments may include a method for assessing the length and offset of the hip of a patient. The method may include placing a guide device including an overlay portion and an alignment portion with at least one contact surface into contact with the femur of a patient. At least two reference points are created at positions at which the contact surface contacts the femur of the patient.

The relative location of the guide device is assessed in comparison to the position of the original femoral head of the patient by marking the overlay portion at a reference point corresponding to the position of the original femoral head. Then, the original femoral head of the patient is removed.

The guide device is positioned on the femur of the patient so the contact surface is aligned on the femur at the previously created reference points. A replacement femoral head is positioned on the femur of the patient so the replacement femoral head aligns with the marking on the overlay portion made at the reference point that corresponds to the position of the original femoral head.

DESCRIPTION OF THE SELECTED EMBODIMENTS

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

Figure 1:
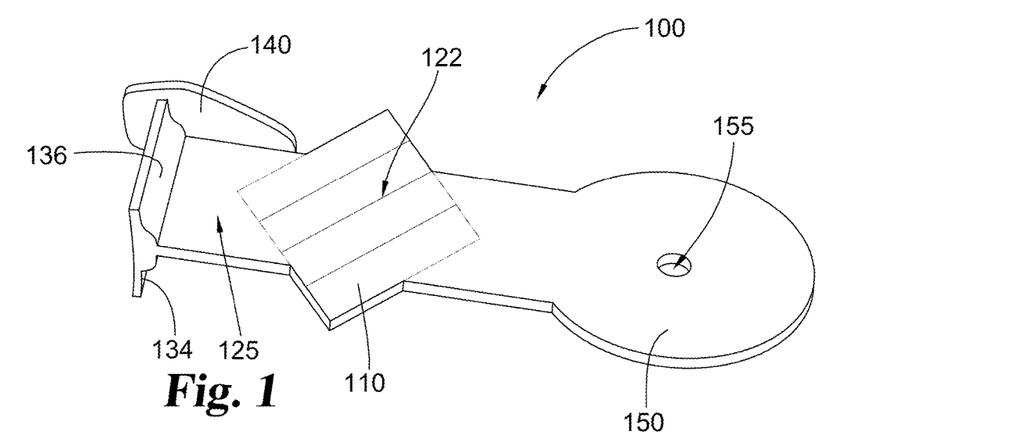
FIG. 1 is a perspective view of an embodiment of a guide device for determining the length and offset of a hip.
Figure 2:
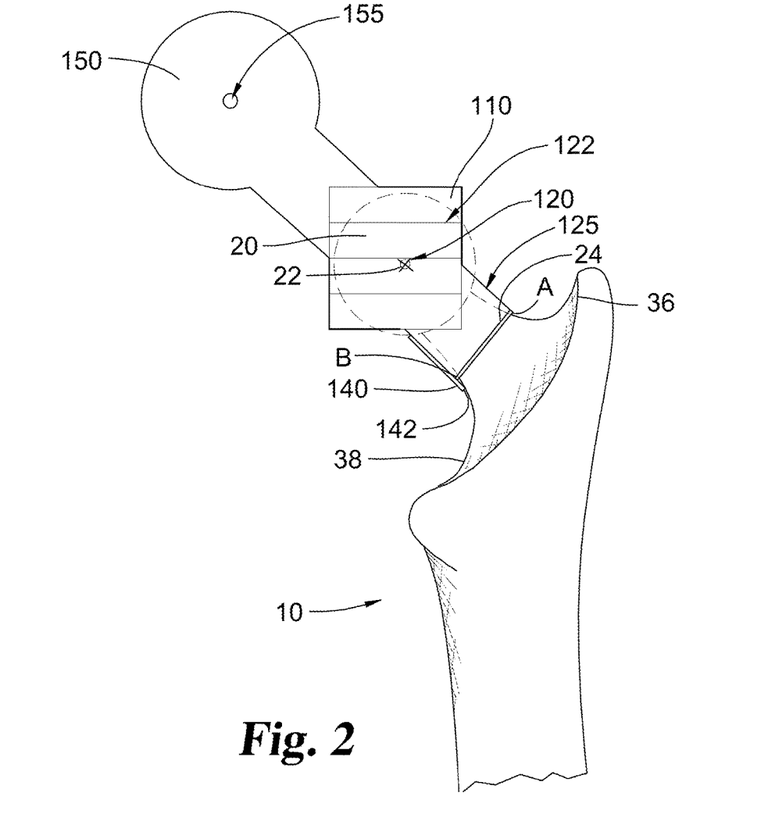
FIG. 2 is a front view of the guide device of FIG. 1 placed on the femur of a patient to determine the relative position of the original femoral head.
Figure 3:
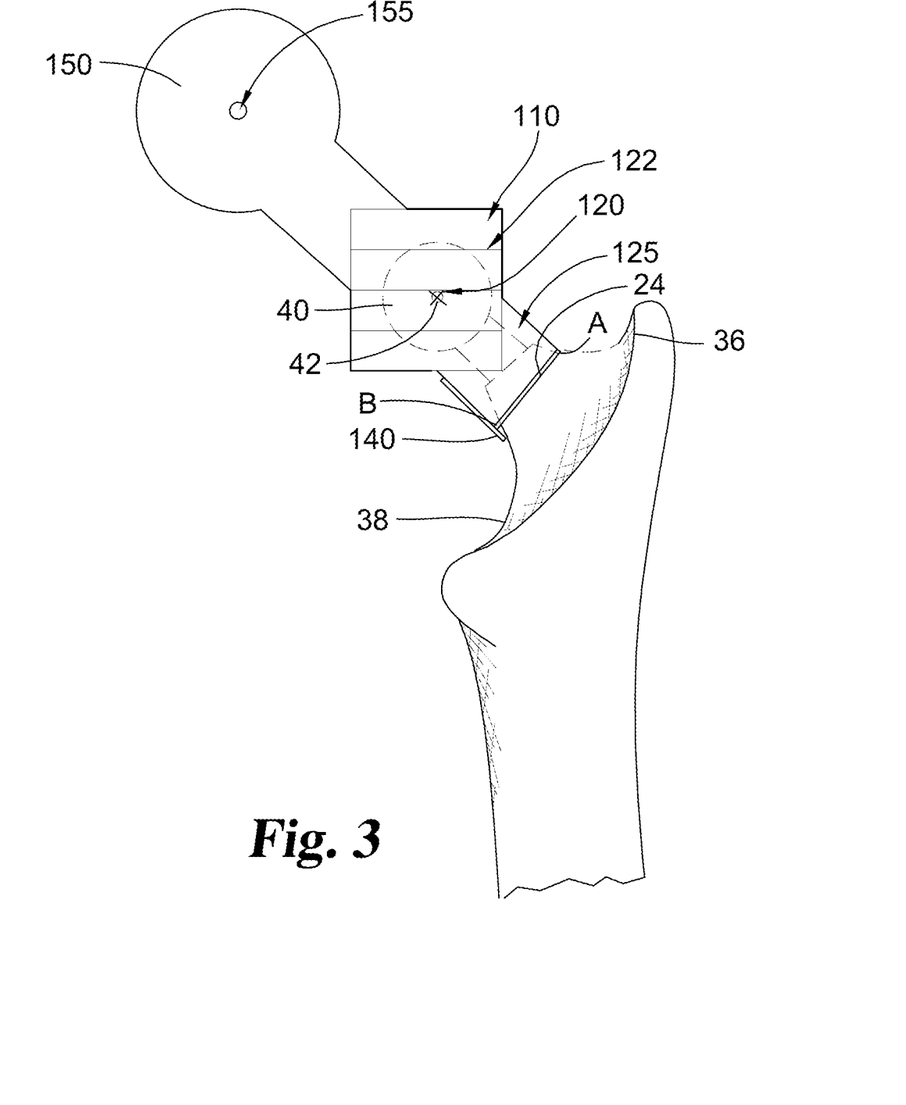
FIG. 3 is a front view of the guide device of FIG. 1 placed on the femur of a patient to determine the relative position of the replacement femoral head.
Figure 4:
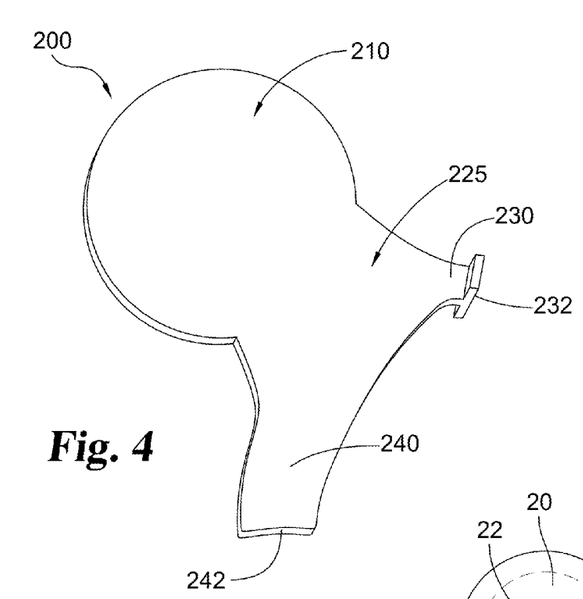
FIG. 4 is a perspective view of an embodiment of a guide device for determining the length and offset of a hip.
Figure 5:
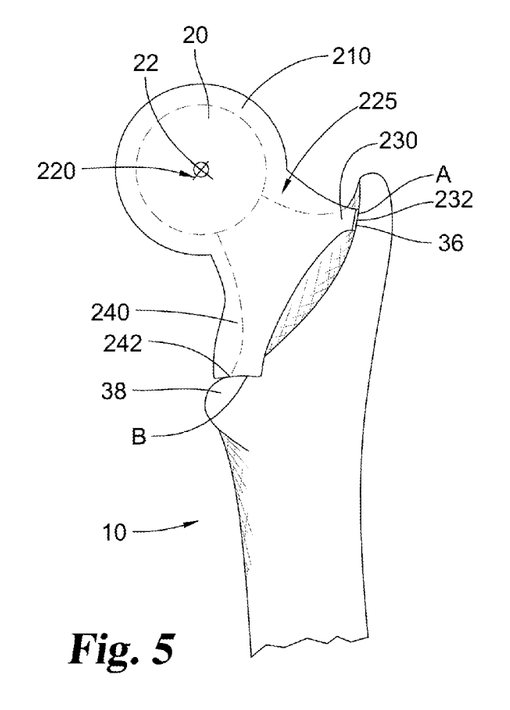
FIG. 5 is a front view of the guide device of FIG. 4 placed on the femur of a patient to determine the relative position of the original femoral head.
Figure 6:
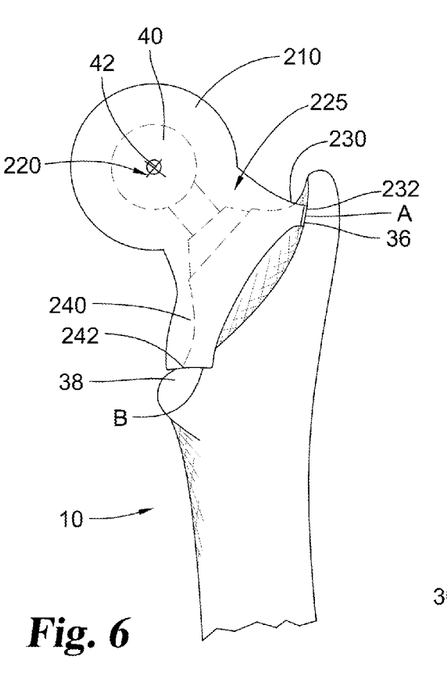
FIG. 6 is a front view of the guide device of FIG. 4 placed on the femur of a patient to determine the relative position of the replacement femoral head.
Figure 7:
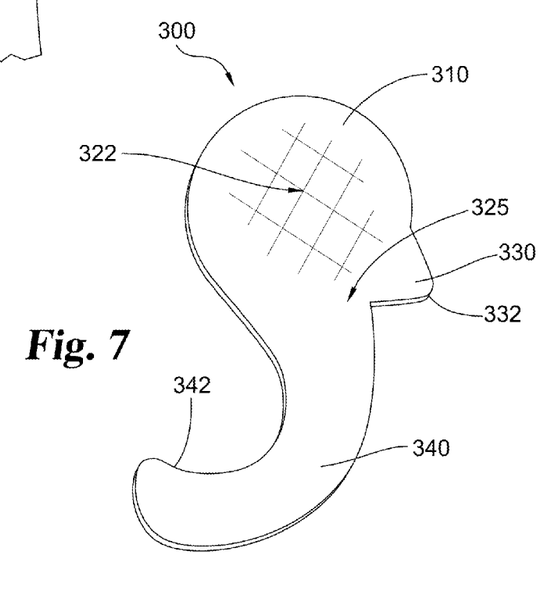
FIG. 7 is a perspective view of an embodiment of a guide device for determining the length and offset of a hip.

With reference to the drawing Figures, for example FIGS. 1-9, a guide device 100, 200, 300 for assessing the length and offset of the hip of a patient is shown. As shown in FIGS. 1, 4, and 7, guide device 100, 200, 300 includes an overlay portion 110, 210, 310 configured to enable assessment of the relative location of the guide device 100, 200, 300 to the original femoral head 20 of a patient (see FIGS. 2, 5 and 8). As an example, the relative location of the guide device to the original femoral head 20 may be determined from the center 22 of the femoral head 20. The relative location of the femoral head 20 may be indicated by a marking 120, 220, 320 on the overlay portion 110, 210, 310.

The guide device also includes an alignment portion 125, including at least one contact surface 134, wherein said contact surface 134 is configured to contact the femur of a patient to create at least two reference points A, B for positioning the guide device 100 on the femur 10.

When the contact surface 134 of alignment portion 125 is positioned at the reference points A, B, the guide device 100 can be used to position a replacement femoral head 40 in the same position as the original femoral head 20 by aligning the replacement femoral head with the marking 120 on the overlay portion 110 (see FIG. 3). As an example, the marking 120 on the overlay portion 110 may be aligned with the center 42 of the replacement femoral head.

As shown in FIGS. 4-6, one feature that is optional, but not required, may be that guide device 200 includes an alignment portion 225 with two legs 230, 240. Leg 230 has a corresponding contact surface 232 and leg 240 has a corresponding contact surface 242. Each contact surface 232, 242 sits on the femur 10 when the guide device 200 is in use to create reference points A, B.

Figure 8:
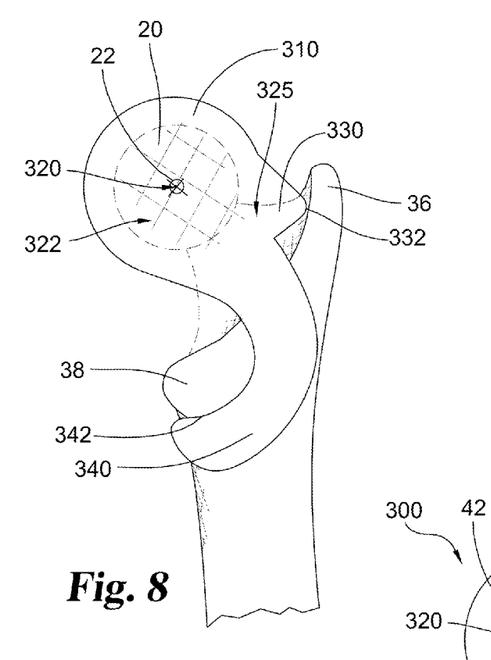
FIG. 8 is a front view of the guide device of FIG. 6 placed on the femur of a patient to determine the relative position of the original femoral head.
Figure 9:
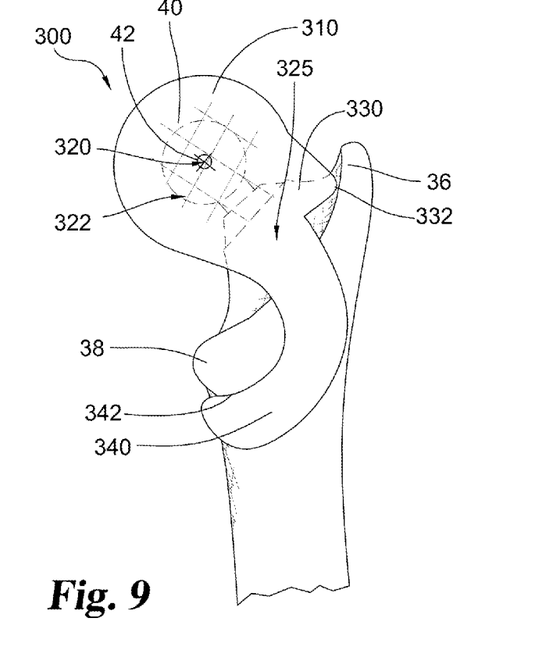
FIG. 9 is a front view of the guide device of FIG. 6 placed on the femur of a patient to determine the relative position of the replacement femoral head.

In another optional embodiment, shown in FIGS. 7-9, guide device 300 includes an alignment portion 325 with two legs 330, 340. Each leg has a corresponding contact surface 332, 342 that makes contact with the femur 10 when guide device 300 is in use. The point at which the contact surfaces 332, 342 contact the femur 10 creates reference points A, B. In this embodiment, leg 342 may be configured to wrap around the lesser trochanter 38 instead of resting on top of the lesser trochanter.

One feature that is optional, but not required, may be that one of the reference points A, B is located at the lesser trochanter 38 of the patient. Alternatively, one of the reference points A, B may be located at the greater trochanter 36 of the patient. In some embodiments, one of the reference points is located at the lesser trochanter 38 of the patient and the other reference point is located at the greater trochanter 36 of the patient.

One feature that is optional, but not required, may be that the overlay portion 110, 210, 310 is made of plastic. Also, in some embodiments, the overlay portion may be transparent.

One feature that is optional, but not required, may be that a support piece 140 is included on one or both of the sides of the alignment portion that may help keep guide device 100 positioned on femur 10. A bottom surface 142 of support piece 140 may contact the femur 10.

One feature that is optional, but not required, may be that the marking made on the overlay portion 110, 210, 310 indicating the relative position of the femoral head 20 is located at a position on the overlay portion corresponding to the center 22 of the original femoral head 20. In some embodiments, the marking on the overlay portion may be created manually, for example, using a marker or by creating an indentation on overlay portion 110, 210, 310. Alternatively, in other embodiments, the marking on the overlay portion may be a line system 122, 322 (see FIGS. 1 and 7) which may be used to assess the location of a desired point of the femoral head. Some embodiments may include multiple markings. For example, a device may include a line system 122, 322 on the surface of the overlay portion and a manually created mark 120, 320 within the line system 122, 132 for determining the relative location of a point of the femoral head.

One feature that is optional, but not required, may be that the overlay portion 110, 210, 310 is configured to allow a user to assess the location of a femoral head 20 of a patient when the overlay portion is positioned between the femoral head 20 and the user (see FIG. 2, 5, or 8).

One feature that is optional, but not required, may be that the guide device 100 includes an extension 150 that is used to determine the center of the femoral head 20. An opening 155 is defined through the center of extension 150. Extension 150 may be aligned with femoral head 20 so opening 155 is positioned at the center of femoral head 20. A user may make a mark on at the center 22 of femoral head 20 through opening 155. This mark may then be used as a reference point when aligning overlay portion 110 with femoral head 20.

In some embodiments of guide device 100 (see FIGS. 1-3), the alignment portion 125 includes a contact surface 134 that extends obliquely from the alignment portion 125 and is configured to be inserted into a groove 24 cut into the femur to create a reference point for positioning the guide device 100. Groove 24 is later deepened to completely remove the original femoral head 20. The guide device 100 can be used to position an artificial femoral head in the same relative position as the original femoral head 20 by positioning contact surface 134 at reference points A, B on the femur at groove 24 and aligning the artificial femoral head with a marking 120 on overlay portion 110.

One feature that is optional, but not required, may be a second contact surface 136 that extends from alignment portion 125. The symmetric design of second contact surface 136 with respect to first contact surface 134 allows guide device 100 to be used on either the left hip or the right hip. In some embodiments, second contact surface 136 may be inserted into groove 24 and be positioned at reference points on the femur.

Figure 10:
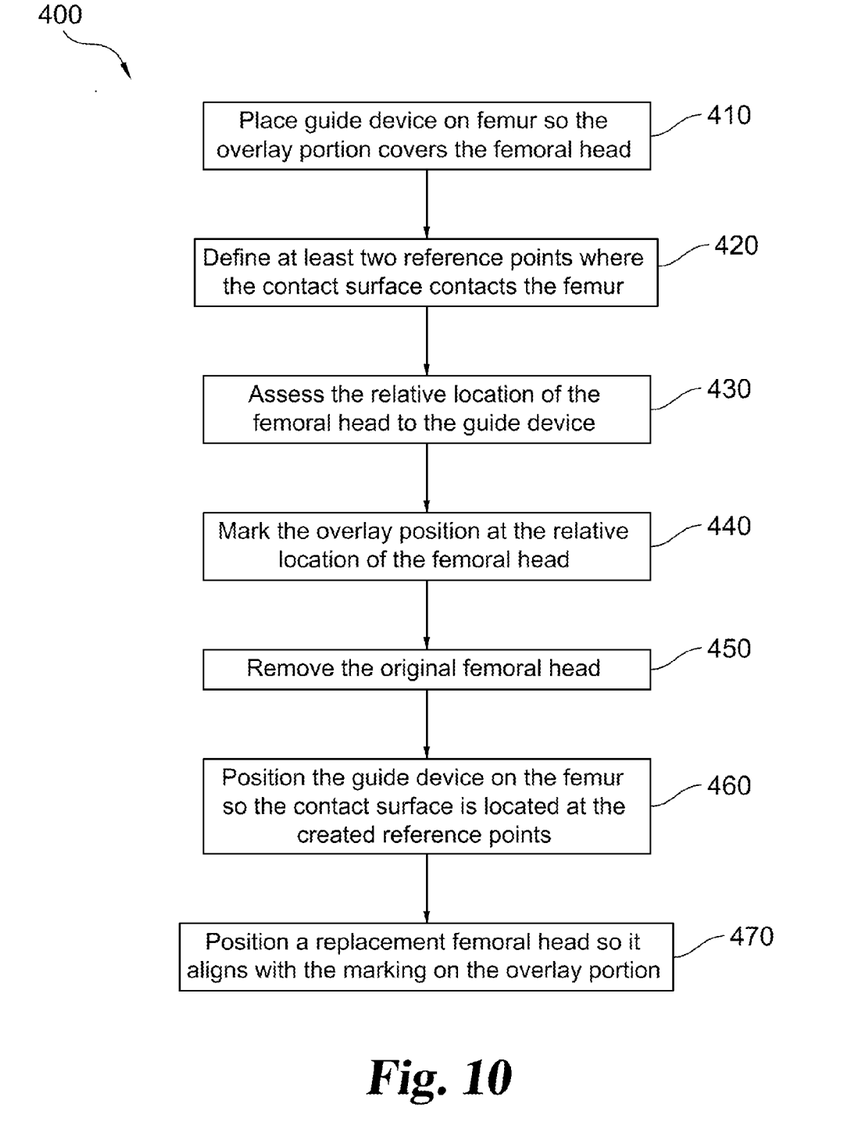
FIG. 10 is a flowchart for an embodiment of a method for assessing the length and offset of a hip of a patient.

A method for assessing the length and offset of a hip of a patient is provided (see FIG. 10). This method 400 may comprise the acts of placing 410 a guide device including an overlay portion and an alignment portion with at least one contact surface into contact with the femur of a patient. At least two reference points are created 420 along the contact surface(s). The relative location of the guide device is assessed 430 in comparison to the position of the original femoral head of a patient. The overlay portion is marked 440 at a reference point corresponding to the position of the original femoral head.

After marking the position of the original femoral head, the femoral head is removed 450. Then the guide device is positioned 460 on the femur of the patient so the contact surface(s) contacts the femur at the reference points. A replacement femoral head is positioned 470 on the femur of the patient so the replacement femoral head aligns with the marking of the reference point on the overlay portion that corresponds to the position of the original femoral head.

One feature that is optional, but not required, is that the position of the original femoral head is assessed using an extension on the guide device. The extension is aligned with the original femoral head and an opening defined through the center of the extension is aligned with the center of the original femoral head. A mark may be made through the opening directly on the original femoral head to assist in aligning the overlay portion with the original femoral head.

One feature that is optional, but not required, may be that one of the reference points is located at the lesser trochanter of the patient, or, optionally, one of the reference points may be located at the greater trochanter of the patient. In some embodiments, one of the reference points is located at the lesser trochanter and the other reference point is located at the greater trochanter of the patient.

One feature that is optional, but not required, may be that there are two distinct contact surfaces. Each of the contact surfaces is placed on the femur at a separate location. Each contact surface may be used to create one of the reference points used to position the replacement femoral head.

One feature that is optional, but not required, may be that one of the reference points is located at the femoral neck near the lesser trochanter of the patient and one of the reference points is located at the femoral neck near the greater trochanter of the patient.

In terms of the meaning of words or terms or phrases herein, literal differences therein are not superfluous and have different meaning, and are not to be synonymous with words or terms or phrases in the same or other claims. As used here (claims, specification, and other definitions) the following terms have the following meaning:

Articles and phases such as, "the", "a", "an", "at least one", and "a first", "comprising", "having" and "including" here are not limited to mean only one, but rather are inclusive and open ended to also include, optionally, two or more of such elements and/or other elements. In terms of the meaning of words or terms or phrases herein, literal differences therein are not superfluous and have different meaning, and are not to be synonymous with words or terms or phrases in the same or other claims.

The term "means for" in a claim invokes 35 U.S.C. § 112(f), literally encompassing the recited function and corresponding structure and equivalents thereto. Its absence does not, unless there otherwise is insufficient structure recited for that claim element. Nothing herein or elsewhere restricts the doctrine of equivalents available to the patentee.

The term "and/or" is inclusive here, meaning "and" as well as "or". For example, "P and/or Q" encompasses, P, Q, and P with Q; and, such "P and/or Q" may include other elements as well.

The term "alignment portion" means here the part of the guide device that is connected to and extends from the overlay portion to engage the femur of the patient.

The term "center of the femoral head" means here the middle point of a patient's femoral head.

The term "contact surface" means here a portion of the guide device that touches the patient's bone when the guide device is in use. A contact surface may be a portion of the guide device that is inserted into a groove, a cut made into the bone, or may be a portion of the guide device that rests on the bone.

The term "extension" means here a portion of the guide device that extends past the overlay portion that may be used to determine the location of the original femoral head and make reference marks at the center of the original femoral head.

The term "femoral head" means here the rounded, articulating portion of the femur. The femoral head is the ball portion of the ball and socket joint that makes up the hip.

The term "femur" means here the thigh bone. The term femur as used includes all portions of the femur, including the femoral head, the neck of the femur, the lesser and greater trochanters, and the body of the femur.

The term "greater trochanter" means here the quadrilateral eminence located at the proximal and lateral portion of the shaft of the femur that provides an attachment point to the gluteus medius and minimus muscles, the piriform muscle, the internal and external obturator muscles, and the gemelli muscles.

The term "groove" means here a narrow cut or depression. A groove may be any man-made cut or naturally occurring opening in the bone that is meant to receive a portion of the guide device to aid in positioning.

The term "leg" means here a part of the alignment portion that includes a surface for contacting the femur. A leg may have any desired length or width and may be any shape that allows the leg to contact the patient's femur.

The term "lesser trochanter" means here a projection from the base of the neck of the femur that receives the insertion of the psoas major and the iliacus muscles.

The term "line system" means here a framework of lines that enable determination of a location. The framework of lines may be parallel lines or may include both parallel and perpendicular lines to form a grid. A line system may be placed on the overlay portion to determine the position of the guide device relative to the femoral head. The line system may be printed on, etched into, or engraved into the overlay portion, or included on the overlay portion by any other suitable method.

The term "manually" means here to be done by a person. As applied to making a marking, the term manually can mean making a marking with a writing utensil such as a marker, making a marking by creating an indentation on the surface of the overlay portion of the guide device, or by any other method a person may perform which makes a visible feature on the overlay portion to indicate a reference position.

The term "marking" means here a visual indication on the overlay portion of the guide device that indicates the position of the femoral head. For example, a marking could be a mark made by a marker at a certain location, such as the center of the femoral head, or could trace the entire femoral head to show its location. The marking could be an indentation or scratch made on the overlay portion. The marking could also be pre-formed, such as a line pattern formed on the overlay portion that shows the position of the femoral head. For example, the user may determine the position of the center of the original femoral head with respect to the line system and align the center of the replacement femoral head with the correct location on the line system.

The term "obliquely" means here positioned at an angle that is neither parallel nor perpendicular.

The term "original femoral head" means here the actual bone of the patient that forms the femoral head before being removed during an arthroplasty procedure.

The term "overlay portion" means here the portion of the guide device that covers the femoral head when the guide device is positioned on the femur. The overlay portion and alignment portion of the guide device may be monolithic or may be separate pieces that are connected. The overlay portion may be made from a different material than the alignment portion. For example, the overlay portion may be made from a clear plastic while the alignment portion is made from steel. The size and shape of the overlay portion may be different for different embodiments. In some embodiments, the overlay portion may be circular, but in other embodiments, the overlay portion may be square, rectangular, or any other desired shape. The overlay portion may be larger than the femoral head of the patient or, in some embodiments, may be smaller than the femoral head of the patient.

The term "physically engage" means here to make contact so the surfaces of the two objects are touching.

The term "reference point" means here a fixed location or a set of fixed locations that are used as the basis for measurement or assessment of the location of another object. As an example, reference points may be located at the positions at which the guide device contacts the portion of the patient's femur that is not removed during the removal procedure. A reference point may also be created on the overlay portion of the guide device.

The term "replacement femoral head" means here a prosthetic femoral head that is attached to the femur during an arthroplasty procedure to replace the original femoral head.

The term "transparent" means here to be clear or to have the property of allowing light to pass through to allow object behind to be distinctly seen.

The invention may include any one or more articles or devices made by any of the claimed methods and/or may by different methods but with a claimed composition.

The language used in the claims and the written description and in the above definitions is to only have its plain and ordinary meaning, except for terms explicitly defined above. Such plain and ordinary meaning is defined here as inclusive of all consistent dictionary definitions from the most recently published (on the filing date of this document) general purpose Webster's dictionaries and Random House dictionaries.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

The invention claimed is:

1. A guide device for assessing the length and offset of a hip of a patient comprising: an overlay portion configured to enable assessment of the relative location of the guide device to the original femoral head of a patient and wherein said relative location is indicated by a marking on said overlay portion; an alignment portion including at least one contact surface integral to said alignment portion and nonplanar with respect to said alignment portion, wherein said contact surface is configured to contact the femur of a patient to create at least two reference points for positioning the guide device on the femur; wherein when said contact surface of said alignment portion is positioned at said reference points, the guide device can be used to position a replacement femoral head in the same position as the original femoral head by aligning the replacement femoral head with said marking on said overlay portion; an extension attached to said overlay portion, wherein at least a portion of said extension is circular in shape to correspond to the shape of a femoral head, and wherein said extension is made of a transparent material so that the original femoral head may be viewed through said extension; and, wherein said extension includes an opening configured to be located at the center of said original femoral head when said extension is aligned with said original femoral head to allow a mark to be made at the center of said original femoral head.

2. The device of claim 1, wherein said overlay portion is transparent.

3. The device of claim 1, wherein said overlay portion is configured to allow a user to assess the location of a femoral head of a patient when said overlay portion is positioned between the femoral head and the user.

4. The device of claim 1, wherein said marking is created manually.

5. The device of claim 1, wherein said marking is located at a position on said overlay portion corresponding to the center of the original femoral head.

6. The device of claim 1, wherein said marking on said overlay portion is a line system.

7. The device of claim 1, wherein the guide device is made of plastic.

8. The device of claim 1, wherein said marking on said overlay portion directly aligns with the center of said original femoral head when said alignment portion is positioned at said reference points.

9. A guide device for assessing the length and offset of a hip of a patient comprising:
   an overlay portion configured to enable assessment of the relative location of the guide device compared to the femoral head of a patient and wherein said relative location is indicated by a marking on said overlay portion;
   an alignment portion configured to physically engage a portion of the femur of the patient, wherein said alignment portion includes a first contact surface and a second contact surface;
   wherein said first contact surface is integral to and extends obliquely from said alignment portion so that said first contact surface is nonplanar with respect to said alignment portion,
   wherein said second contact surface extends from a side of said alignment portion opposite said first contact surface and wherein said second contact surface is nonplanar with respect to said alignment portion;
   wherein either of said first contact surface or said second contact surface is of limited thickness to be configured to be inserted into a groove cut into the femur to create a reference point for positioning the guide device; and
   wherein the guide device can be used to position an artificial femoral head in the same relative position as the original femoral head by positioning said contact surface at said reference point on the femur and aligning the artificial femoral head with said marking on said overlay portion.

10. The device of claim 9, further comprising:
    an extension attached to said overlay portion, wherein said extension includes an opening configured to be located at the center of said original femoral head when said extension is aligned with said original femoral head.

11. The device of claim 9, wherein said overlay portion is transparent.

12. The device of claim 9, wherein said overlay portion is configured to allow a user to assess the location of a femoral head of a patient when said overlay portion is positioned between the femoral head and the user.

13. The device of claim 9, wherein said marking on said overlay portion directly aligns with the center of said original femoral head when said contact surface is inserted into said groove.

* * * * *